(12) United States Patent
Tadepalli et al.

(10) Patent No.: US 11,873,277 B2
(45) Date of Patent: Jan. 16, 2024

(54) CIRCULAR ECONOMIC METHODS FOR FRAGRANCE INGREDIENTS (71) Applicant: International Flavors & Fragrances Inc., New York, NY (US)

(72) Inventors: Sunitha R. Tadepalli, Morganville, NJ (US); Paul Daniel Jones, Aberdeen, NJ (US); Geatesh K. Tampy, Colts Neck, NJ (US); John P. Cherkauskas, Burlington, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 0 days.

(21) Appl. No.: 17/578,515

(22) PCT Filed: Jul. 27, 2020

(86) PCT No.: PCT/US2020/043660
§ 371 (c)(1),
(2) Date: Jan. 19, 2022

(87) PCT Pub. No.: WO2021/021694
PCT Pub. Date: Feb. 4, 2021

(65) Prior Publication Data
US 2022/0324778 A1    Oct. 13, 2022

Related U.S. Application Data (60) Provisional application No. 62/879,012, filed on Jul. 26, 2019.

(51) Int. Cl.
*C07C 6/12* (2006.01)
*C07C 5/27* (2006.01)
*C07C 5/41* (2006.01)

(52) U.S. Cl.
CPC ............ *C07C 6/123* (2013.01); *C07C 5/2737* (2013.01); *C07C 5/41* (2013.01); *C07C 2521/08* (2013.01); *C07C 2529/08* (2013.01); *C07C 2529/40* (2013.01)

(58) Field of Classification Search
CPC ......... C07C 6/123; C07C 5/2737; C07C 5/41; C07C 2521/08; C07C 2529/08; C07C 2529/40; C07C 5/373; C07C 2521/04; C07C 2523/44; C07C 5/367; C07C 2527/126; C07C 2529/70; C07C 5/2751; C07C 4/18; C07C 4/12
See application file for complete search history.

(56) References Cited

U.S. PATENT DOCUMENTS

2013/0130345 A1* 5/2013 Thai ...................... C07C 51/265
435/166

* cited by examiner

*Primary Examiner* — Thuan D Dang (57) ABSTRACT

Disclosed is a method for converting cymene generated from renewable low value terpene streams into renewable benzene, toluene, xylenes, and cymene isomers (ortho and meta) under flow disproportionation reaction conditions, which compounds are basic building blocks for fragrance materials. This technology has potential to replace high volume petrochemical-based feedstocks with plant-based building blocks that can fill the renewability gap for key fragrance ingredients.

21 Claims, 5 Drawing Sheets

CIRCULAR ECONOMIC METHODS FOR FRAGRANCE INGREDIENTS

CROSS-REFERENCE TO RELATED APPLICATION

This application claims priority to U.S. Application Ser. No. 62/879,012 filed Jul. 26, 2019, the content of which is incorporated by reference in its entirety.

FIELD OF THE INVENTION

The present invention is related to the field of renewable aromatic fragrance ingredients and to a general method for the production of aromatic building blocks from renewable sources.

BACKGROUND OF THE INVENTION

Aromatics, particularly benzene, toluene, and xylenes (ortho, meta, and para isomers), which are commonly referred to as "BTX," are extremely useful chemicals in the petrochemical, chemical, fragrance and many other industries. In the fragrance industry, they represent the building blocks for many fragrance ingredients including, without limitation, benzaldehyde, benzyl alcohol, salicylates, musk GX, musk indanone, rose absolute pentanol, benzoates and many others. Conventionally, BTX compounds are obtained by separation and processing of fossil-fuel petroleum fractions, for example, in catalytic reforming or cracking refinery process units, followed by processing through BTX recovery units. Alternatively, trans-alkylation and disproportionation reactions are commonly practiced in the petrochemical industry for converting toluene and trimethyl benzenes to benzene and xylenes (see, for example, U.S. Pat. Nos. 5,367,009, 5,173,461 and 4,962,257). Trans-alkylation of p-cymene with benzene to produce cumene and toluene has been reported as well in US20130130345A1.

With a goal of leading positive transformational changes toward a regenerative, healthy and abundant world, the concept of a circular economy has been embraced. Consumers are increasingly demanding products that are environmentally and socially responsible, with general health and well-being as central elements. Given this focus on a circular economy, it is important to create products and processes that are restorative and regenerative by design. By using renewable carbon sources, a significant contribution to such a circular economy can be made, thus reducing the use of fossil feedstocks.

There have been several initiatives by various groups related to biomass conversion to aromatic compounds based on different renewable feedstocks. However, there continues to be a need for a new and simple economic process to prepare such BTX building blocks from renewable resources.

SUMMARY OF THE INVENTION

The present invention meets this need and demand. More specifically, aspects presented herein relate to converting cymene derived from terpentines, fusel oil waste, tire industrial waste and/or citrus waste into BTX building blocks.

One such aspect provides methods of converting to produce BTX aromatics in high yields under flow disproportionation reaction conditions. The renewable cymenes (ortho, meta, and para isomers) are typically derived from monoterpenes such as limonene, phellandrene, pinene, camphene, carene, terpinene, cineol, borneol, carveol and mixtures thereof.

In some aspects of the present invention, the monoterpenes can be converted to renewable cymenes by contacting monoterpenes with a dehydrogenation catalyst under conditions effective to produce cymenes and hydrogen. See Scheme I below. The catalyst system can be a heterogeneous catalyst system selected from the group consisting of Pd/C, Pd/Alumina, Pd/CG, Pt/C, Pt/Alumina, Molybdenum Oxide, Vanadium Pentoxide, Rh/Alumina, Ru/Al$_2$O$_3$, Bismuth Molybdate, Zeolites and combinations thereof. In some embodiments, the reaction is conducted in a first flow reactor, preferably in the presence of an inert gas such as nitrogen, helium and mixtures thereof. The first flow reaction (i.e., the dehydrogenation reaction) can be carried out at a temperature ranging from about 60° C. to about 600° C., preferably from about 200° C. to about 600° C. This flow reaction is typically performed with a Weight Hourly Space Velocity (WHSV) from about 0.5 hr$^{-1}$ to about 10 hr$^{-1}$.

Another aspect of this invention related to a process for producing a renewable aromatic backbone compound or a mixture thereof, comprising the step of contacting a renewable cymene with a suitable catalyst under flow disproportionation reaction conditions effective to convert the cymene to the renewable aromatic backbone compound selected from the group consisting of toluene, benzene, cymene isomers, xylenes and combinations thereof. The catalyst and flow disproportionation reaction conditions can be selected so that the renewable cymene produces a mixture of renewable toluene and propylene.

In one aspect, the present invention provides methods of converting cymenes into toluene and a mixture of cymenes in one step, through tandem dealkylation of cymene and alkylation of toluene.

In another aspect, the present invention provides methods of converting cymene into toluene, benzene and xylene in one step, through tandem dealkylation of cymene and disproportionation of toluene.

In a preferred embodiment, the present invention provides methods of converting cymene into toluene, benzene and xylene in the presence of hydrogen, nitrogen or a mixture thereof.

Scheme I limonene  β-phellandrene

α-terpinene  γ-terpinene

β-pinene  camphene

In another aspect, the present invention provides methods of converting cymene primarily to toluene and propylene in one step, through dealkylation of cymene in the presence of nitrogen. These aspects are diagramed in Scheme II below.

The catalyst and flow disproportionation reaction conditions can be selected so that renewable cymene produces a mixture of renewable toluene and propylene. The catalyst can be an acidic zeolite catalyst. The acidic zeolite can be selected from the group consisting of ZSM-5, zeolite Y, beta zeolite, Sn on beta zeolite, lithium on beta zeolite, and combinations of two or more thereof. The term "ZSM-5" refers to Zeolite Socony Mobil-5, an aluminosilicate zeolite belonging to the pentasil family of zeolites. Its chemical formula is $Na_nAl_nSi_{96-n}O_{192} \cdot 16H_2O$ (0<n<27). This flow disproportionation reaction (i.e., the second flow reaction) can be carried out in the presence of an inert gas such as nitrogen, helium and mixtures thereof.

Also within the scope of this invention is a process for producing an aromatic backbone compound, comprising the following steps: a) contacting a monoterpene with a dehydrogenation catalyst under conditions effective to produce a cymene and hydrogen in a first flow reactor, and b) contacting the cymene with a disproportionation catalyst in a second flow reactor under conditions effective to convert the cymene to an aromatic backbone compound or its mixture, wherein the aromatic backbone compound is selected from the group consisting of toluene, benzene, cymene isomers, and xylenes. The catalyst and reaction conditions are described above and also below in detail.

DETAILED DESCRIPTION OF THE INVENTION

As disclosed herein, a number of ranges of numeric values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention. The term "about" generally includes up to plus or minus 10% of the indicated number. For example, "about 10%" may indicate a range of 9% to 11%, and "about 20" may mean from 18 to 22. Preferably "about" includes up to plus or minus 6% of the indicated value. Alternatively, "about" includes up to plus or minus 5% of the indicated value. Other meanings of "about" may be apparent from the context, such as rounding off, so, for example "about 1" may also mean from 0.5 to 1.4.

One aspect of the invention relates to a process for producing renewable cymenes by contacting monoterpenes with a dehydrogenation catalyst in a first continuous flow reactor (i.e., the first reaction). Another aspect of the invention relates to converting the renewable cymenes in a second continuous flow reactor (i.e., the second reaction).

As used herein, the phrase "cymene" or "cymenes" refers to ortho cymene, meta cymene, para cymene and mixture thereof.

As used herein, the phrase "reactor" refers to a device where the reaction occurs. As used herein, the term "continuous reactor" refers to a flow reactor operated in a continuous mode versus a batch mode.

The catalyst for producing cymenes is preferably a heterogenous catalyst such as Pd/C, Pd/Alumina, Pd/CG, Pt/C, Pt/Alumina, Molybdenum Oxide, Vanadium Pentoxide, Rh/Alumina, Ru/Al$_2$O$_3$, Bismuth Molybdate, Silica, Alumina, Zeolites, or a combination of two or more thereof.

In some aspects, the process for producing cymenes is represented, without limitation, by the following experimental procedures and accompanying figures.

In some aspects, the reaction is carried out in a temperature range from about 60° C. to about 600° C., preferably about 200° C. to about 600° C.

In some aspects, the Weight Hourly Space Velocity (WHSV) through the reactor is about 0.5 to about 10 hr$^{-1}$. The term "Weight Hourly Space Velocity" refers to the weight of feed (e.g., terpentines and cymenes) flowing into the reactor per unit weight of the catalyst per hour.

Another aspect of the invention relates to a process for producing aromatic backbone compounds comprising reacting cymene in the presence of a solid catalyst in a second continuous flow reactor (the second reaction).

The catalyst for producing aromatic backbones is preferably an acidic catalyst, such as a zeolite, including, without limitation, ZSM-5, zeolite Y, beta zeolite, Sn on beta zeolite, lithium on beta zeolite, or a combination of two or more thereof.

As used herein, the phrase "aromatic backbones" or "aromatic backbone compounds" refers to benzene, toluene, xylenes, cymenes and/or mixture thereof.

In some embodiments of the present invention, the flow reactor (either the first or second reactor) may be a packed bed reactor, where the reactor is packed with solid materials such as a catalyst or catalysts, and optionally a catalyst support. As used herein, the terms "packed" and "packing" mean to fill with an amount of material that allows effective and efficient production of benzene, toluene, xylenes and cymenes, and the amount of material often requires taking into consideration such factors as the size of the reactor vessel, the type and particle size of the packing material, and the pre-determined desired quantity of aromatic backbone compounds.

Figure 1:
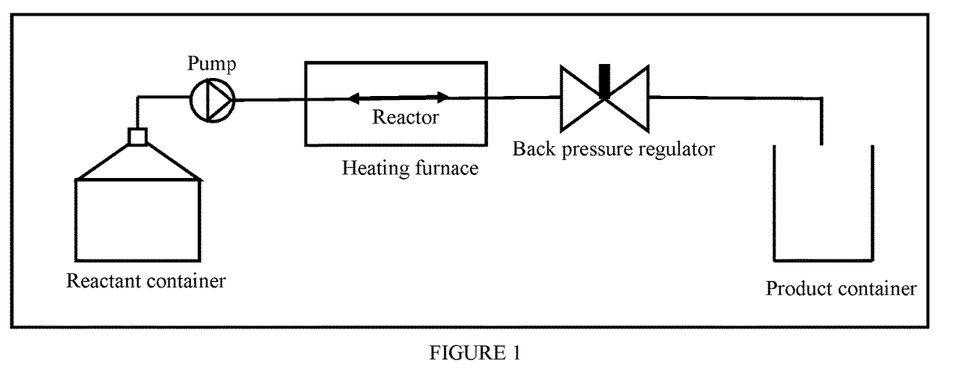
FIG. 1 shows a diagram for a general flow reactor system for dehydrogenation of terpenes and production of aromatic backbone compounds.

In some embodiments, the liquid stream containing the reactant, for example, cymene or monoterpene, is pumped into the reactor system (either the first or second reactor) containing catalyst and the reactor is pressurized using a back pressure regulator or a compressor as shown in FIG. 1. In other embodiments, the reactant is mixed with an inert gas using a static mixer before entering the reactor system, for example, the reactor system depicted in FIG. 2. In still other embodiments, the reactant is mixed with an inert gas and/or hydrogen using a static mixer and is run under pressure using a compressor or back pressure regulator as depicted in FIG. 3. In some aspects, the reactor configuration can be a combination of the systems illustrated in FIGS. 1, 2 and/or 3. In some aspects, the reactor system may comprise a catalyst retainer to prevent the catalyst from moving out of the reactor. In some aspects, the reactor system is heated using a heating means or device, such as an electric heater. After flowing through the reactor system, the reaction mixture can be collected in a product receiver. The reaction mixture can be analyzed using a suitable analytical technique, such as, for example, gas chromatography (GC).

In some aspects, the first or second reaction, independently, is carried out in the presence of an inert gas including, without limitation, nitrogen, helium or a mixture thereof.

In some aspects, the second reaction is carried out in the presence of hydrogen, with hydrogen pressure ranging from 1 to 50 atmospheres.

In some aspects, the second reaction is carried out with hydrogen-to-cymene molar ratio of about 0.1 to about 10, preferably between about 2 and about 6.

In some aspects, the second reaction is carried out in a temperature range from about 60° C. to about 600° C., preferably about 300° C. to about 600° C.

In some aspects, the Weight Hourly Space Velocity (WHSV) through the second reactor is about 0.5 to about 10 hr$^{-1}$.

In a preferred aspect, the present invention provides methods of converting cymene into toluene, benzene and xylene in the presence of hydrogen, nitrogen or mixtures thereof. Thus, a preferred embodiment is the flow disproportionation reaction of cymene carried out in the presence of nitrogen, hydrogen or a combination thereof as described above. Flow disproportionation in the presence of hydrogen provides a solution to the issue of catalyst deactivation. Minimizing or avoiding such catalyst deactivation is critical for successful implementation of a commercially viable process. Flow disproportionation in the presence of nitrogen can also be used to change the product distribution between toluene and benzene, according to the type of aromatic building blocks required.

EXAMPLES

The following examples serve to illustrate the invention, without restricting its scope in any way.

Comparative Example 1: Liquid Phase Disproportionation Reaction of Para Cymene with Standard Lewis Acid Catalysts—Aluminum Chloride (Laboratory Scale)

A mixture of about 2 g of para-cymene and 0.1 g of anhydrous aluminum chloride was heated to 60° C. for 5 hours. At the end of 5 hours, the reaction mixture was quenched with water and the resulting organic layer was analyzed by GC and GCMS. The product showed a mixture of cymene isomers (67.6%), toluene (10.8%) and methyl di-isopropyl benzene isomers (20.8%). Para-cymene has a by of 177.10° C.; meta-cymene has a bp of 175.14° C.; and ortho-cymene has a bp of 178.15° C.

Example 2: Flow Reaction of Cymene with Solid Catalysts Under Pressure

A number of solid catalysts were evaluated for the disproportionation reaction of para-cymene in the fixed bed reactor system depicted in FIG. 1. P-cymene was fed into the reactor at 0.1 mL/min (Example 2c) or 0.2 mL/min (Examples 2a, ab, and 2d) with a temperature of 450° C. (Example 2a) or 500° C. (Examples 2b-d) in the reactor. The molar ratio of silicon to aluminum is 19:1 in all three catalysts. The reactor was packed with 2.25 g (Examples 2a and 2b) or 2.5 g (Examples 2c and 2d) of a catalyst. In Examples 2a and 2b, H-beta zeolite was used as the catalyst. In Example 2c, Sn-beta zeolite was used. In Example 2d, ZMS was used. The downstream pressure was kept at 600 psi (Examples 2a and 2b) or 650 psi (Example 2d). The resulting product mixtures formed using various catalysts and conditions are summarized in Table 1.

TABLE 1

Catalyst Screening of Flow Disproportionation Reaction

| | | Product Composition (%) | | | | | |
|---|---|---|---|---|---|---|---|
| | WHSV | toluene | xylenes | benzene | lights | p-cymene | Other cymene isomers |
| 2a | 4.57 | 29 | 2.1 | 1.5 | 4.3 | 10.9 | 21.7 |
| 2b | 4.57 | 14.9 | 0.6 | 0.4 | 0.9 | 42 | 20 |
| 2c | 2.06 | 54.5 | | 0.2 | | 10.9 | 25 |
| 2d | 4.11 | 26.2 | | 7.5 | | 33.8 | 0 |

The data show that when H-beta zeolite and Sn-beta zeolite were used, the major products are toluene and cymene isomers. This result indicates that cymene is first dealkylated to form toluene and propylene, which react again under pressure to form cymene isomers. With ZSM-5 catalyst, the primary products are benzene, toluene and p-cymene. In this case, the toluene formed from dealkylation of cymene undergoes further disproportionation to benzene and xylenes.

Example 3: Flow Reaction of Cymene with Different Catalysts and Nitrogen

Figure 2:
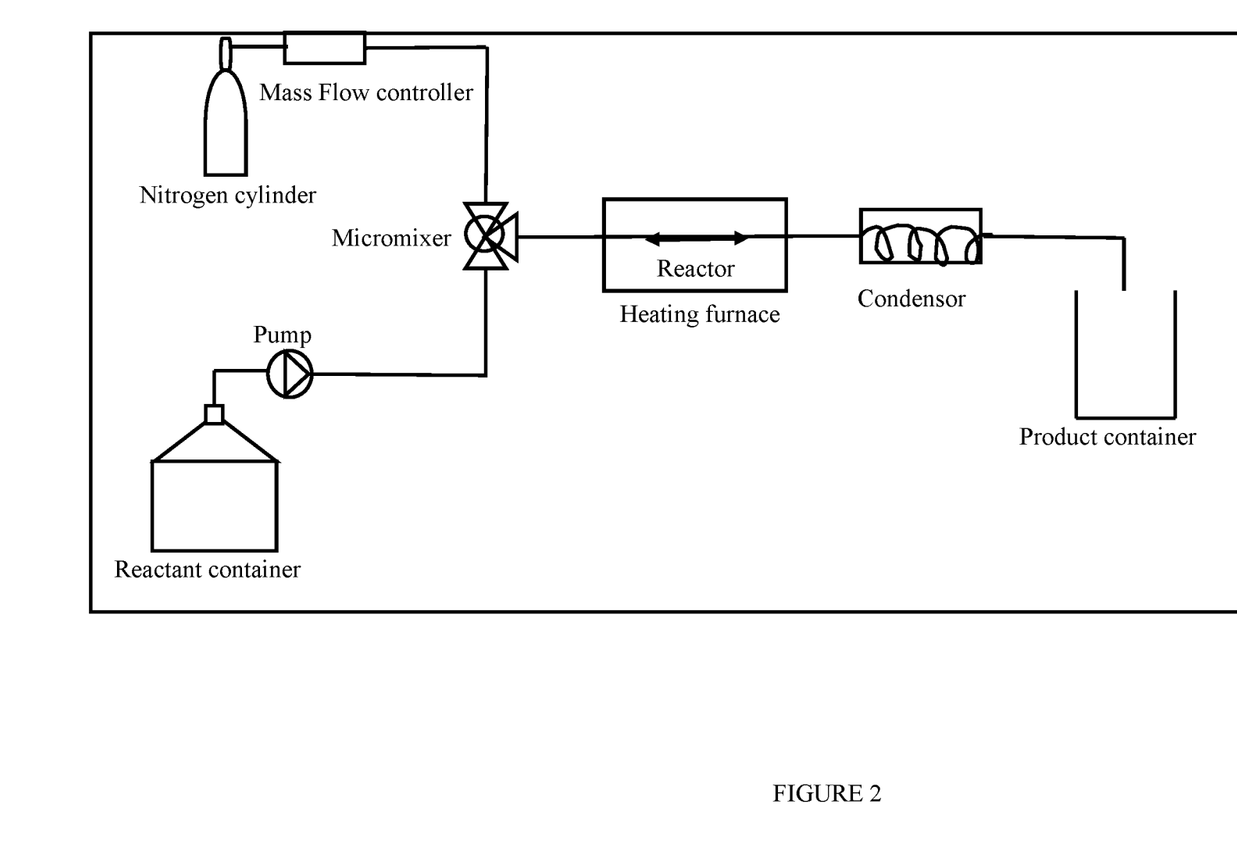
FIG. 2 shows a diagram of a representative flow reactor system for dehydrogenation of terpenes and production of aromatic backbone compounds using nitrogen.
Figure 3:
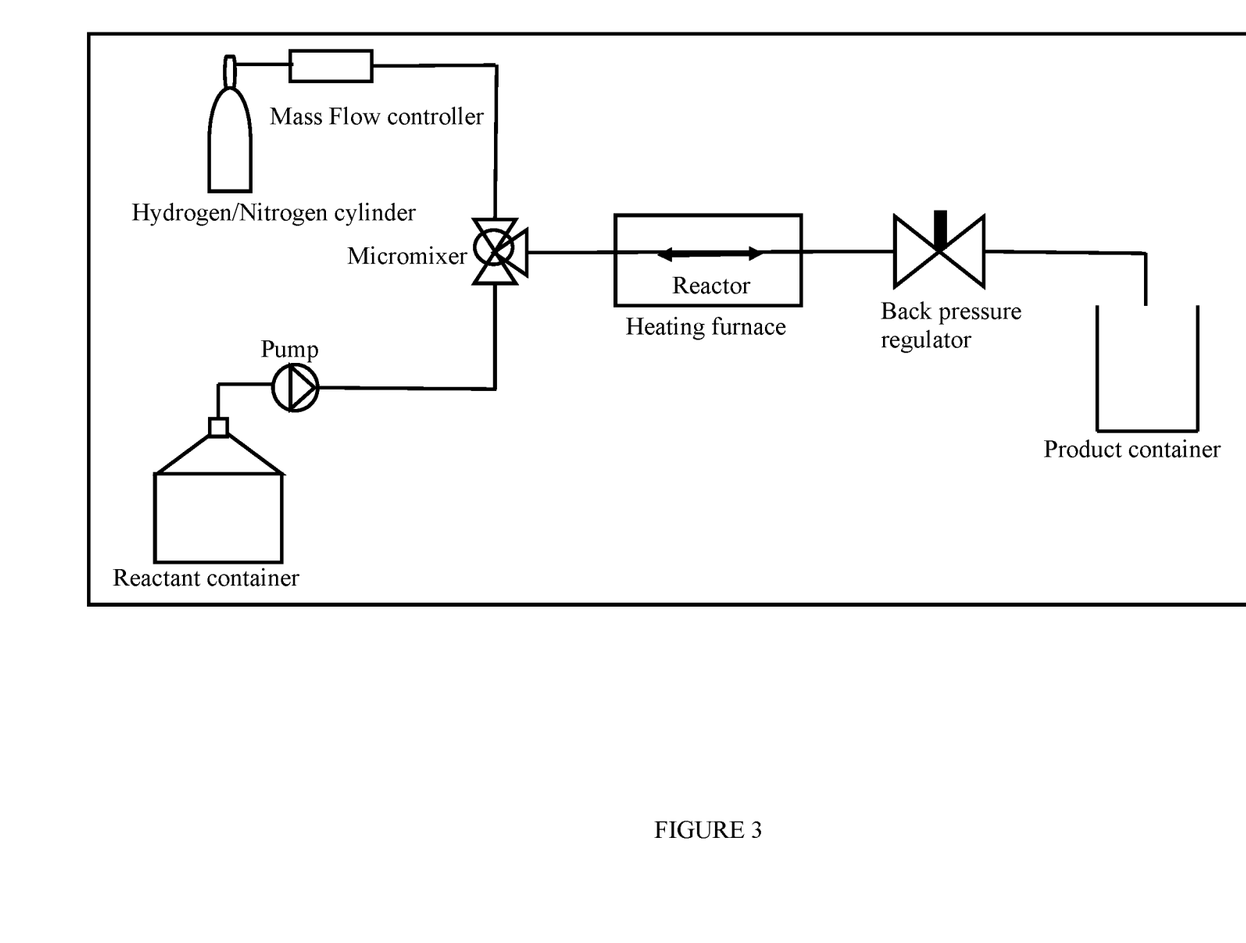
FIG. 3 shows a diagram of a representative flow reactor system for production of aromatic backbone compounds using hydrogen or a mixture of hydrogen in nitrogen.

A number of solid zeolite catalysts were evaluated for the cymene disproportionation reaction in the fixed bed flow reactor system depicted in FIG. 2, in the presence of nitrogen fed into the reactor at 5 mL/min. P-cymene was fed into the reactor at 0.1 mL/min. The reaction conditions were summarized in Table 2 below.

The product mixtures were analyzed. The weight % of each product in the reaction mixture are summarized in Table 3 below.

TABLE 2

| | Temp (° C.) | Catalyst | Si/Al | Catalyst Weight (g) | WHSV |
|---|---|---|---|---|---|
| 3a | 450 | Sn-beta | 19 | 2.5 | 2.06 |
| 3b | 400 | Li-beta | 19 | 3.931 | 1.31 |
| 3c | 450 | Li-beta | 19 | 3.931 | 1.31 |
| 3d | 500 | Li-beta | 19 | 3.931 | 1.31 |
| 3e | 500 | Ga-ZSM-5 | 19 | 2.951 | 1.74 |
| 3f | 450 | ZSM-5 | 19 | 3.101 | 1.66 |
| 3g | 500 | ZSM-5 | 19 | 3.101 | 1.66 |
| 3h | 550 | ZSM-5 | 19 | 3.101 | 1.66 |
| 3i | 550 | ZSM-5 | 11.5 | 3.329 | 1.54 |

TABLE 3

| | toluene | xylenes | benzene | lights | p-cymene | cymene isomers |
|---|---|---|---|---|---|---|
| 3a | 72.3 | | 2.5 | | 2.7 | 3.4 |
| 3b | 57 | 4.8 | 4.1 | 7.4 | 4 | 7.6 |
| 3c | 66.1 | 1.7 | 1.9 | 11.5 | 3.8 | 5.3 |
| 3d | 74.7 | 2.3 | 1.9 | 6 | 1.9 | 3.3 |
| 3e | 36.8 | 0.4 | 0.1 | 4.3 | 49.2 | 2.5 |
| 3f | 60.6 | | 6.6 | | 1.3 | 0.5 |
| 3g | 57.4 | | 10.2 | | 7.1 | 0.4 |
| 3h | 50.2 | | 15.2 | | 1 | |
| 3i | 42.6 | 12.1 | 25.1 | 1.7 | 0.3 | 0.2 |

In the presence of nitrogen, Sn-beta, Li-beta and Ga/ZSM-5 catalysts formed toluene as the major product from dealkylation of cymene. Under certain conditions, the produced toluene was as high as about 75%. The gas stream liberated during the reaction was also collected under dry ice conditions into hexanes, and the dissolved organics were analyzed by GC, being identified as propylene for the Li-beta catalyst. Similar to example 2, with ZSM-5 catalyst the primary products were benzene, toluene and xylenes, with production of as much as 25% benzene.

Example 4: Flow Reaction with Various Catalysts and Hydrogen

Figure 4:
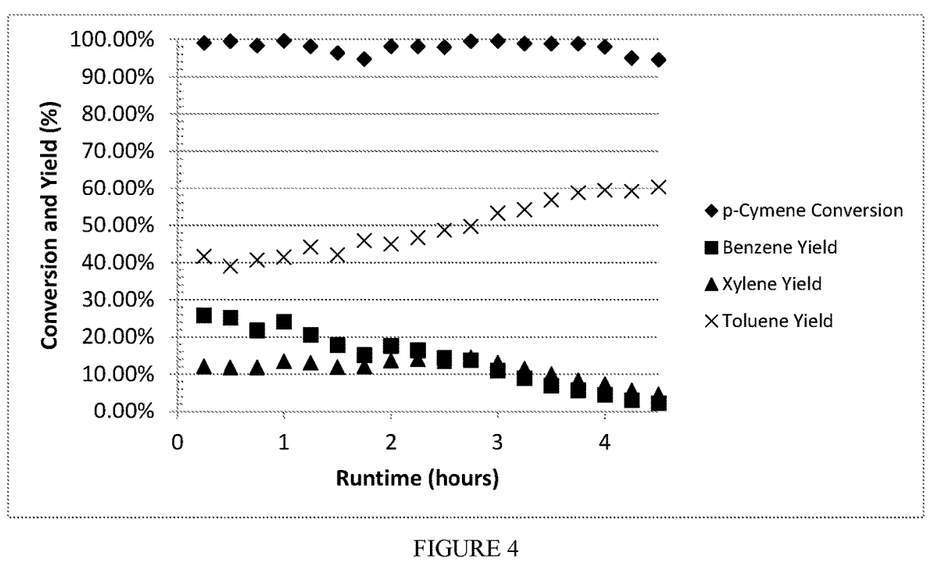
FIG. 4 shows a graph of reaction composition (% conversion/% yield) as a function of time using ZSM-5 catalyst in the presence of nitrogen.
Figure 5:
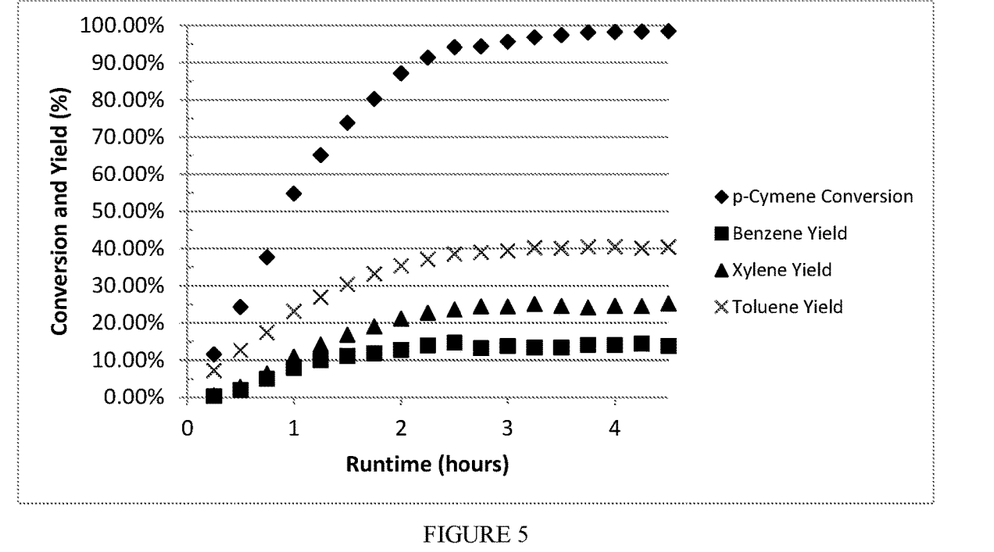
FIG. 5 shows a graph of p-cymene disproportionation, (% conversion/% yield) vs. time, demonstrating that catalyst activity is maintained in the presence of hydrogen.

A major issue with using ZSM-5 catalyst for disproportion reactions is catalyst deactivation during the course of the reaction due to coking. Similar issues were also observed with ZSM-5 during the disproportionation of cymene, as evidences by FIG. 4. Literature reports indicate that catalyst activity can be maintained by incorporating hydrogen gas in the feed (Technology, Oil & Gas Journal, Aug. 21, 1989, pp 83-88). Based on this precedent, the disproportionation of cymene was also evaluated with hydrogen using the reactor configuration depicted in FIG. 3. P-cymene was fed at 0.1 mL/min to the reactor, which was packed with ZSM-5. The downstream pressure was kept at 400 psi. The reaction was carried out according to the conditions in Table 4 below. The product mixtures formed in the presence of hydrogen are summarized in Table 5. The presence of hydrogen provides more stable catalyst activity as a function of time (as evidenced by FIG. 5).

TABLE 4

| | Molar ratio of $N_2/H_2$, flow (mL/min) | Temp (° C.) | Si/Al | Cat (g) | WHSV |
|---|---|---|---|---|---|
| 4a | 96/4, 15 | 400 | 12.5 | 4.133 | 1.24 |
| 4b | 0/100, 31 | 550 | 11.5 | 3.459 | 1.49 |

TABLE 5

| | toluene | xylenes | benzene | lights | p-cymene | Other cymene isomers |
|---|---|---|---|---|---|---|
| 4a | 24.3 | 8.8 | 4.4 | 2.7 | 41.4 | 1.3 |
| 4b | 33.8 | 18.4 | 15.7 | | 12.3 | 1 |

Example 5: Dehydrogenation of Terpenes with Solid Catalyst

Dehydrogenation of terpenes to cymene was evaluated in the fixed bed reactor system depicted in FIG. 2. A mixture of terpenes, primarily rich in Limonene and phellandrene was fed into the reactor at 0.5 mL/min, in the presence of nitrogen at 10 ml/min with a temperature of 300° C. in the reactor. The reactor was packed with 12 g of 5% Palladium on Alumina catalyst. The resulting product show >96% of para cymene.

Example 6: Dehydrogenation of Terpenes with Solid Catalyst

Dehydrogenation of terpenes to cymene was evaluated in the fixed bed reactor system depicted in FIG. 2. A mixture of terpenes, primarily rich in delta carene was fed into the reactor at 0.05 mL/min with a temperature of 425° C. in the reactor. The reactor was packed with 4 g of Silica catalyst. The resulting product show 20% of a mixture of meta and para-cymene, 16% of limonene isomers and 37% of remaining starting material.

In summary, one aspect of the invention is directed to a process for producing a mixture of renewable aromatic backbone compounds, comprising the step of contacting renewable cymene with a suitable catalyst, under flow disproportionation reaction conditions which are effective to convert the cymene to a mixture of renewable toluene, benzene, cymene isomers, and xylenes. The catalyst and flow reaction conditions can be selected so that renewable cymene produces a mixture of renewable toluene and propylene. The catalyst is preferably a solid acidic catalyst, such as an acidic zeolite catalyst selected from the group consisting of ZSM-5, zeolite Y, beta zeolite, Sn on beta zeolite, lithium on beta zeolite, and combinations of two or more thereof.

The flow disproportionation reaction of the process can be carried out in the presence of an inert gas. The inert gas can be selected from nitrogen, helium or nitrogen-helium mixtures. In one aspect, the flow disproportionation reaction of the process is carried out in the presence of hydrogen gas. The hydrogen gas pressure can be about 1 to about 50 atmospheres. In one aspect, the flow disproportionation reaction of the process can be carried out in the presence of nitrogen gas. In one aspect, the flow disproportionation reaction of the process can be carried out in the presence of a nitrogen-hydrogen gas mixture.

The hydrogen-to-cymene molar ratio of the process can be about 0.1 to about 10, preferably about 2 to about 6, more preferably about 3 to about 5. The H:cymene ratio can be about 0.1, or about 0.3, or about 0.5, or about 0.7, or about 0.9, or about 1, or about 1.5, or about 2, or about 2.5, or about 3, or about 3.5, or about 4, or about 4.5, or about 5, or about 4.5, or about 5, or about 5.5, or about 6, or about 6.5, or about 7, or about 7.5, or about 8, or about 8.5, or about 9, or about 9.5, or about 10.

The flow reaction (either the first or second flow reaction) of the process can be carried out at a temperature ranging from about 60° C. to about 600° C.; preferably the flow reaction temperature ranges from about 300° C. to about 600° C., more preferably about 400° C. to about 500° C. The flow reaction temperature can be about 60° C., or about 70° C., or about 80° C., or about 90° C., or about 100° C., or about 150° C., or about 200° C., or about 250° C., or about 300° C., or about 350° C., or about 400° C., or about 450° C., or about 500° C., or about 550° C., or about 600° C.

The flow reaction (either the first or second flow reaction) of the process can be carried out with a Weight Hourly Space Velocity (WHSV) from about 0.5 to about 10 $hr^{-1}$, preferably about 1 to about 5 $hr^{-1}$, more preferably about 1.2 to about 4.6 $hr^{-1}$. The WHSV can be about 0.5 $hr^{-1}$, or about 0.6 $hr^{-1}$, or about 0.7 $hr^{-1}$, or about 0.8 $hr^{-1}$, or about 0.9 $hr^{-1}$, or about 1.0 $hr^{-1}$, or about 1.2 $hr^{-1}$, or about 1.4 $hr^{-1}$, or about 1.6 $hr^{-1}$, or about 1.8 $hr^{-1}$, or about 2.0 $hr^{-1}$, or about 2.5 $hr^{-1}$, or about 3.0 $hr^{-1}$, or about 3.5 $hr^{-1}$, or about 4.0 $hr^{-1}$, or about 4.5 $hr^{-1}$, or about 5.0 $hr^{-1}$, or about 5.5 $hr^{-1}$, or about 6.0 $hr^{-1}$, or about 6.5 $hr^{-1}$, or about 7.0 $hr^{-1}$, or about 7.5 $hr^{-1}$, or about 8.0 $hr^{-1}$, or about 8.5 $hr^{-1}$, or about 9.0 $hr^{-1}$, or about 9.5 $hr^{-1}$, or about 10 $hr^{-1}$.

All publications cited herein are incorporated by reference in their entirety for all purposes.

It will be understood by those of skill in the art that numerous and various modifications can be made without departing from the spirit of the present invention. Therefore, it should be clearly understood that the various embodiments of the present invention described herein are illustrative only and are not intended to limit the scope of the present invention in any way. Descriptions of features or aspects within each embodiment should typically be considered as available for other similar features or aspects in other embodiments.

What is claimed is:

1. A process for producing a renewable aromatic backbone compound or a mixture thereof, comprising the step of contacting a renewable cymene with a suitable catalyst under flow disproportionation reaction conditions effective to convert the cymene to the renewable aromatic backbone compound selected from the group consisting of toluene, benzene, cymene isomers, xylenes and combinations thereof,
    wherein the catalyst and flow disproportionation reaction conditions are selected so that the renewable cymene produces a mixture comprising renewable toluene and propylene.

2. The process of claim 1, wherein the catalyst is an acidic zeolite catalyst.

3. The process of claim 2, wherein the acidic zeolite is selected from the group consisting of ZSM-5, zeolite Y, beta zeolite, Sn on beta zeolite, lithium on beta zeolite, and combinations of two or more thereof.

4. The process of claim 2, wherein the flow disproportionation reaction is carried out in the presence of an inert gas.

5. The process of claim 4, wherein the inert gas is selected from the group consisting of nitrogen, helium and mixtures thereof.

6. The process of claim 2, wherein the flow disproportionation reaction is carried out in the presence of a hydrogen gas.

7. The process of claim 6, where the hydrogen gas pressure is about 1 to about 50 atmospheres.

8. The process of claim 6, wherein the hydrogen-to-cymene molar ratio is about 0.1 to about 10.

9. The process of claim 8, wherein the hydrogen-to-cymene molar ratio is about 2 to about 6.

10. The process of claim 2, wherein the flow disproportionation reaction is carried out at a temperature ranging from about 60° C. to about 600° C.

11. The process of claim 10, wherein the flow disproportionation reaction temperature ranges from about 300° C. to about 600° C.

12. The process of claim 2, wherein the flow disproportionation reaction is carried out with a Weight Hourly Space Velocity (WHSV) from about 0.5 to about 10 $hr^{-1}$.

13. A process for producing a renewable aromatic backbone compound or a mixture thereof, comprising the step of contacting a renewable cymene with a suitable catalyst under flow disproportionation reaction conditions effective to convert the cymene to the renewable aromatic backbone compound selected from the group consisting of toluene, benzene, cymene isomers, xylenes and combinations thereof, wherein the catalyst is an acidic zeolite catalyst, and the flow disproportionation reaction is carried out in the presence of an inert gas and/or a hydrogen gas.

14. The process of claim 13, wherein the acidic zeolite is selected from the group consisting of ZSM-5, zeolite Y, beta zeolite, Sn on beta zeolite, lithium on beta zeolite, and combinations of two or more thereof.

15. The process of claim 13, wherein the inert gas is selected from the group consisting of nitrogen, helium and mixtures thereof.

16. The process of claim 13, where the hydrogen gas pressure is about 1 to about 50 atmospheres.

17. The process of claim 13, wherein the hydrogen-to-cymene molar ratio is about 0.1 to about 10.

18. The process of claim 17, wherein the hydrogen-to-cymene molar ratio is about 2 to about 6.

19. The process of claim 13, wherein the flow disproportionation reaction is carried out at a temperature ranging from about 60° C. to about 600° C.

20. The process of claim 19, wherein the flow disproportionation reaction temperature ranges from about 300° C. to about 600° C.

21. The process of claim 13, wherein the flow disproportionation reaction is carried out with a Weight Hourly Space Velocity (WHSV) from about 0.5 to about 10 $hr^{-1}$.

* * * * *